US011344207B2

(12) United States Patent
Kato et al.

(10) Patent No.: US 11,344,207 B2
(45) Date of Patent: May 31, 2022

(54) PRESSURE PULSE WAVE SENSOR AND BIOLOGICAL INFORMATION MEASUREMENT DEVICE

(71) Applicant: OMRON HEALTHCARE Co., Ltd., Kyoto (JP)

(72) Inventors: Yuki Kato, Kyoto (JP); Noriko Shigihara, Kyoto (JP); Masayuki Wakamiya, Kyoto (JP); Toshihiko Ogura, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 500 days.

(21) Appl. No.: 15/893,469

(22) Filed: Feb. 9, 2018

(65) Prior Publication Data

US 2018/0160919 A1 Jun. 14, 2018

Related U.S. Application Data

(63) Continuation of application No. PCT/JP2016/073325, filed on Aug. 8, 2016.

(30) Foreign Application Priority Data

Aug. 24, 2015 (JP) .............................. JP2015-164697

(51) Int. Cl.
*A61B 5/021* (2006.01)
*A61B 5/022* (2006.01)
(Continued)

(52) U.S. Cl.
CPC ............ *A61B 5/02108* (2013.01); *A61B 5/02* (2013.01); *A61B 5/022* (2013.01); *A61B 5/02233* (2013.01); *A61B 5/681* (2013.01)

(58) Field of Classification Search
CPC .............................. A61B 5/02108; A61B 5/02
See application file for complete search history.

(56) References Cited

U.S. PATENT DOCUMENTS 5,101,829 A * 4/1992 Fujikawa ............... A61B 5/022
600/485
5,131,400 A * 7/1992 Harada .................. A61B 5/021
600/500
(Continued)

FOREIGN PATENT DOCUMENTS

CN 101547634 A 9/2009
CN 104540450 A 4/2015
(Continued)

OTHER PUBLICATIONS

Fahim, M., Bijwe, J., & Nalwa, H. S. (2001). Polyimides for Microelectronics and Tribology Applications. Supramolecular Photosensitive and Electroactive Materials, 643-726. doi: 10.1016/b978-012513904-5/50010-7 (Year: 2001).*
(Continued)

*Primary Examiner* — Allen Porter
*Assistant Examiner* — Yasmeen S Warsi
(74) *Attorney, Agent, or Firm* — Osha Bergman Watanabe & Burton LLP (57) ABSTRACT

A pressure pulse wave sensor includes: a sensor chip including: a pressure-sensitive element row configured by a plurality of pressure-sensitive elements arranged in one direction; and a chip-side terminal portion placed in an end portion in the one direction of a pressure-sensitive surface on which the pressure-sensitive element row is formed, and electrically connected to the pressure-sensitive element row; and a substrate including a concave portion, the sensor chip fixed to a bottom surface of the concave portion, a substrate-side terminal portion for being electrically connected to the chip-side terminal portion is disposed on a surface of the
(Continued)

substrate in which the concave portion is formed, and the pressure pulse wave sensor further includes: an electroconductive member connecting the chip-side terminal portion and the substrate-side terminal portion to each other; and a protective member covering the electroconductive member.

12 Claims, 3 Drawing Sheets

(51) Int. Cl.
*A61B 5/02* (2006.01)
*A61B 5/00* (2006.01)

(56) References Cited

U.S. PATENT DOCUMENTS

| | | | | |
|---|---|---|---|---|
| 5,179,956 | A * | 1/1993 | Harada | A61B 5/02233 600/485 |
| 5,797,850 | A * | 8/1998 | Archibald | A61B 5/021 600/494 |
| 6,293,915 | B1 * | 9/2001 | Amano | A61B 5/021 600/485 |
| 2005/0016289 | A1 | 1/2005 | Saito et al. | |
| 2006/0047207 | A1 | 3/2006 | Itonaga et al. | |
| 2010/0076328 | A1 | 3/2010 | Matsumura et al. | |
| 2015/0201875 | A1 | 7/2015 | Tateda et al. | |
| 2016/0310021 | A1 | 10/2016 | Kato et al. | |

FOREIGN PATENT DOCUMENTS

| | | |
|---|---|---|
| JP | H03-186247 A | 8/1991 |
| JP | H06-090912 A | 4/1994 |
| JP | 2000-287944 A | 10/2000 |
| JP | 2004-188183 A | 7/2004 |
| JP | 2004-361308 A | 12/2004 |
| JP | 2007-301232 A | 11/2007 |
| JP | 2015-144628 A | 8/2015 |

OTHER PUBLICATIONS

Jia, M., Wu, C., Li, W., & Gao, D. (2009). Synthesis and characterization of a silicone resin with silphenylene units in Si—O—Si backbones. Journal of Applied Polymer Science, 114(2), 971-977. doi: 10.1002/app.30635 (Year: 2009).*

Xie, W., Pan, W.-P., & Chuang, K. C. (2001). Thermal characterization of PMR polyimides. Thermochimica Acta, 367-368, 143-153. doi: 10.1016/s0040-6031(00)00698-5 (Year: 2001).*

Extended European Search Report issued in European Application No. 16839077.1, dated Jan. 28, 2019 (8 pages).

International Search Report issued in Application No. PCT/JP2016/073325, dated Sep. 6, 2016 (3 pages).

Written Opinion issued in Application No. PCT/JP2016/073325, dated Sep. 6, 2016 (4 pages).

International Preliminary Report on Patentability issued in Application No. PCT/JP2016/073325, dated Dec. 12, 2017 (9 pages).

Office Action issued in corresponding Chinese Application No. 201680047186.3, dated May 28, 2020 (17 pages).

* cited by examiner

PRESSURE PULSE WAVE SENSOR AND BIOLOGICAL INFORMATION MEASUREMENT DEVICE

CROSS-REFERENCE TO RELATED APPLICATION(S)

This application is a continuation of PCT application No. PCT/JP2016/073325, which was filed on Aug. 8, 2016 based on Japanese Patent Application (No. 2015-164697) filed on Aug. 24, 2015, the contents of which are incorporated herein by reference.

BACKGROUND

1. Technical Field

The present invention relates to a pressure pulse wave sensor and a biological information measurement device.

2. Background Art

Usually, a press type pressure measurement device is known which measures a contact pressure against an object to be measured, while applying a pressure against the object to be measured. As a device to which such a press type pressure measurement device is applied, there is a pulse wave measurement device.

A pulse wave measurement device is a device which, in order to measure a pressure pulse wave that is generated in an artery located in a position which is relatively shallow from the skin of a living body, measures the pressure pulse wave while pressing a substrate having a pressure-sensitive element against the body surface. In order to know the health condition of a subject, it is very important to measure the pressure pulse wave of the subject by using such a pulse wave measurement device.

In such a press type pulse wave measurement device, it is usual to employ a sensor chip which uses a distortion gauge and a diaphragm, as a pressure-sensitive element. For example, JP-A-2007-301232 and JP-A-2004-188183 disclose this kind of press type pulse wave measurement device.

JP-A-2007-301232 discloses a pulse wave measurement device that measures a pressure pulse wave by using a pressure sensor chip in which pressure-sensitive elements are two-dimensionally arranged.

JP-A-2004-188183 discloses a pulse wave detection device on which a pressure sensor chip in which a diaphragm is formed in a planar semiconductor substrate, and electric terminals on the surface of the semiconductor substrate are connected to those on a flexible substrate by a brazing material is mounted.

The diaphragm has a configuration where a plurality of pressure-sensitive elements are arranged in one direction, wirings extend from each of the pressure-sensitive elements toward both sides in a perpendicular direction that is perpendicular to the one direction, and the flexible substrate is connected to end portions of the wirings.

Although not related to a press type pressure measurement device, JP-A-2000-287944 and JP-A-2004-361308 relate to a pressure measurement device which measures a fluid pressure.

JP-A-2000-287944 discloses a catheter in which a chip accommodating concave portion is disposed in the catheter body, and the bottom surface of the chip accommodating concave portion is formed as a mounting surface for a pressure sensor chip. In the catheter, in one end of the longitudinal direction of the pressure sensor chip, a diaphragm (distortion gauge circuit) of the pressure sensor chip, and a wiring portion of a flexible substrate are connected to each other by wire bonding.

JP-A-2004-361308 discloses a pressure detecting apparatus which uses a pressure sensor chip having a diaphragm mounted on a semiconductor substrate, thereby measuring an engine intake pressure of an automobile.

A pressure sensor chip which is used in a pulse wave measurement device is pressed against the skin in a state where a pressure-sensitive element row in which a plurality of pressure-sensitive elements are arranged in one direction intersects the traveling direction of an artery. In the pulse wave measurement device, the pressure sensor chip is located above the artery as described above, the optimum pressure-sensitive element and the optimum pressing force are determined, and thereafter a pressure pulse wave is detected based on a signal that is output from the optimum pressure-sensitive element at the optimum pressing force.

In a pressure sensor chip which is to be used in a pulse wave measurement device, in order to determine the optimum pressure-sensitive element, therefore, the detection sensitivities of plural pressure-sensitive elements are requested to be made uniform so that all of the pressure-sensitive elements can detect a pressure pulse wave under the same conditions.

In the case where a pressure sensor chip including the pressure-sensitive element row, and a substrate on which wiring terminals for being connected to electric terminals of the pressure sensor chip are electrically connected to each other by wire bonding or the like, connecting portions (in the case where the connection is performed by wire bonding, wires) between the substrate and the pressure sensor chip must be protected by a protective member such as a resin.

In this case, when the protective member which protects wirings for connecting the pressure sensor chip with the substrate is deformed by the temperature or the humidity, a compression stress or a tensile stress is sometimes applied to the pressure sensor chip depending on a change of the environment.

When a compression stress or a tensile stress is generated in this way, the detection sensitivities of the pressure-sensitive elements of the pressure-sensitive element row are sometimes dispersed, thereby causing a problem in that it becomes difficult to accurately measure a pressure pulse wave.

JP-A-2007-301232 fails to disclose a specific configuration of the pressure sensor chip, and cannot solve the above-described problem.

The pressure sensor chip described in JP-A-2004-188183 has a configuration where the wirings extend from each of the pressure-sensitive elements of the pressure-sensitive element row toward the both sides of a direction perpendicular to the direction in which the pressure-sensitive element row elongates, and the flexible substrate is connected to the end portions of the wirings. In the case where a connecting portion between the pressure sensor chip and the substrate is protected by, for example, a resin, when the resin is deformed, a compression stress or a tensile stress acts on the pressure-sensitive element row.

In the configuration, however, the wiring protective resin is disposed on the both sides of each of the pressure-sensitive elements, and therefore the pressure-sensitive elements receive an influence of the stress in a substantially uniform manner. Namely, the possibility in which, in the pressure-sensitive element row, the detection sensitivities are largely dispersed is low. Therefore, JP-A-2004-188183 lacks recognition of the above-described problem.

In JP-A-2000-287944, the use of plural pressure-sensitive elements, and the detection of a pressure pulse wave are not supposed. Therefore, JP-A-2000-287944 lacks recognition of the above-described problem.

In JP-A-2004-361308, the detection of a pressure pulse wave is not supposed. Therefore, JP-A-2004-361308 lacks recognition of the above-described problem.

SUMMARY

The invention has been conducted in view of the above circumstances. It is an object of the invention to provide a pressure pulse wave sensor in which the accuracy of detecting a pressure pulse wave can be prevented from being lowered due to a change of the use environment, and a biological information measurement device which includes the sensor.

According to an aspect of the invention, there is provided a pressure pulse wave sensor comprising: a sensor chip which includes: a pressure-sensitive element row configured by a plurality of pressure-sensitive elements that are arranged in one direction; and a chip-side terminal portion that is placed in an end portion in the one direction of a pressure-sensitive surface on which the pressure-sensitive element row is formed, and that is electrically connected to the pressure-sensitive element row, the sensor chip to be used while the pressure-sensitive surface is pressed against a body surface of a living body in a state where the one direction intersects a traveling direction of an artery of the living body; and a substrate which includes a concave portion, the sensor chip fixed to a bottom surface of the concave portion, a substrate-side terminal portion for being electrically connected to the chip-side terminal portion is disposed on a surface of the substrate in which the concave portion is formed, and the pressure pulse wave sensor further includes: an electroconductive member which connects the chip-side terminal portion and the substrate-side terminal portion to each other; and a protective member which covers the electroconductive member.

According to an aspect of the invention, there is also provided a biological information measurement device comprising: the pressure pulse wave sensor; and a biological information calculating section which is configured to calculate biological information based on a pressure pulse wave detected by the pressure pulse wave sensor.

DESCRIPTION OF EXEMPLARY EMBODIMENTS

Hereinafter, an embodiment of the invention will be described with reference to the drawings.

Figure 1:
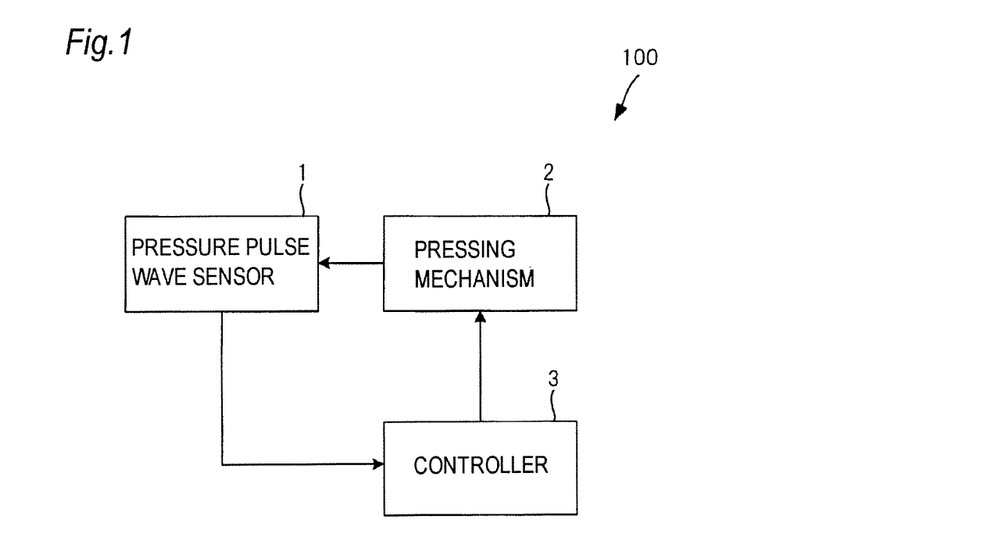
FIG. 1 is a block diagram showing the configuration of a blood pressure measurement device 100 which is a biological information measurement device for illustrating an embodiment of the invention.

FIG. 1 is a block diagram showing the configuration of a blood pressure measurement device 100 which is a biological information measurement device for illustrating an embodiment of the invention. For example, the blood pressure measurement device 100 is of the wrist wearing type which is used while attached to the wrist.

The blood pressure measurement device 100 includes: pressure pulse wave sensors 1; a pressing mechanism 2 for pressing the pressure pulse wave sensor 1 against the body surface of the subject; and a controller 3 which controls the pressing mechanism based on a signal output from the pressure pulse wave sensors 1, and which calculates biological information including the blood pressure of the subject, based on the signal.

Figure 2:
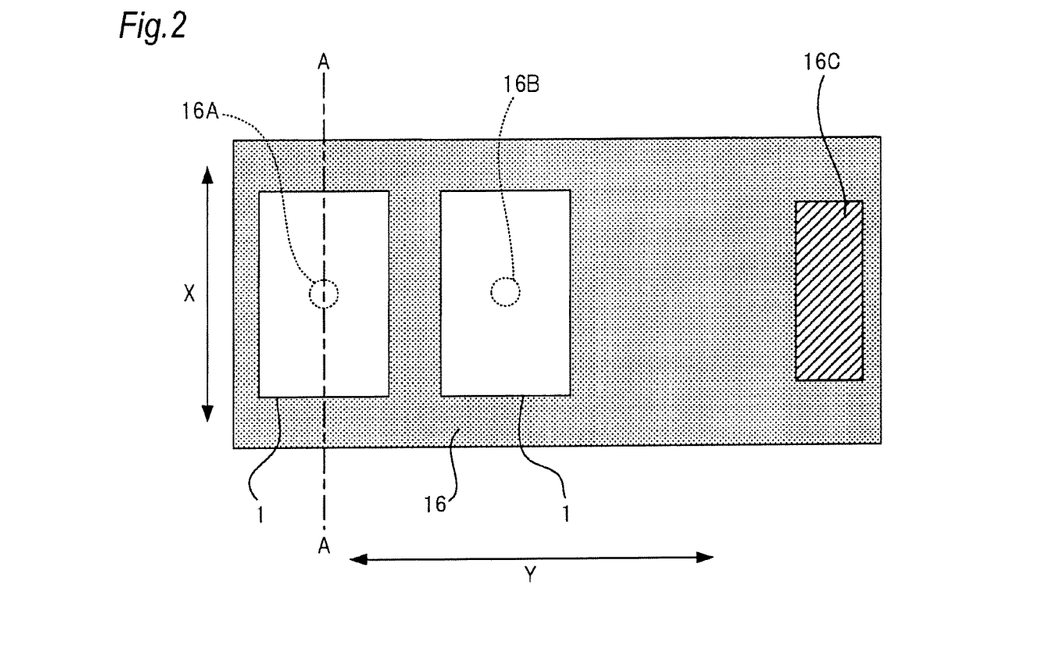
FIG. 2 is a plan view of a flexible substrate 16 on which pressure pulse wave sensors 1 of FIG. 1 are mounted.

FIG. 2 is a plan view of a flexible substrate 16 on which the pressure pulse wave sensors 1 shown in FIG. 1 are mounted.

The flexible substrate 16 is formed into a rectangular shape in which a direction Y perpendicular to a direction X that is one direction coincides with the longitudinal direction. Two pressure pulse wave sensors 1 and a connector 16C are mounted on the surface of the substrate.

In the flexible substrate 16, wirings connected respectively to electric terminals of the two pressure pulse wave sensors 1 are disposed in a resin film. The wirings are led to the connector 16C. The connector 16C is connected to a connector of a circuit board which is not shown, and on which the controller 3 of FIG. 1 and the like are formed.

Moreover, the flexible substrate 16 has through holes 16A, 16B in substantially middles of regions where the two pressure pulse wave sensors 1 are mounted, respectively. The through holes 16A, 16B will be described later.

Figure 3:
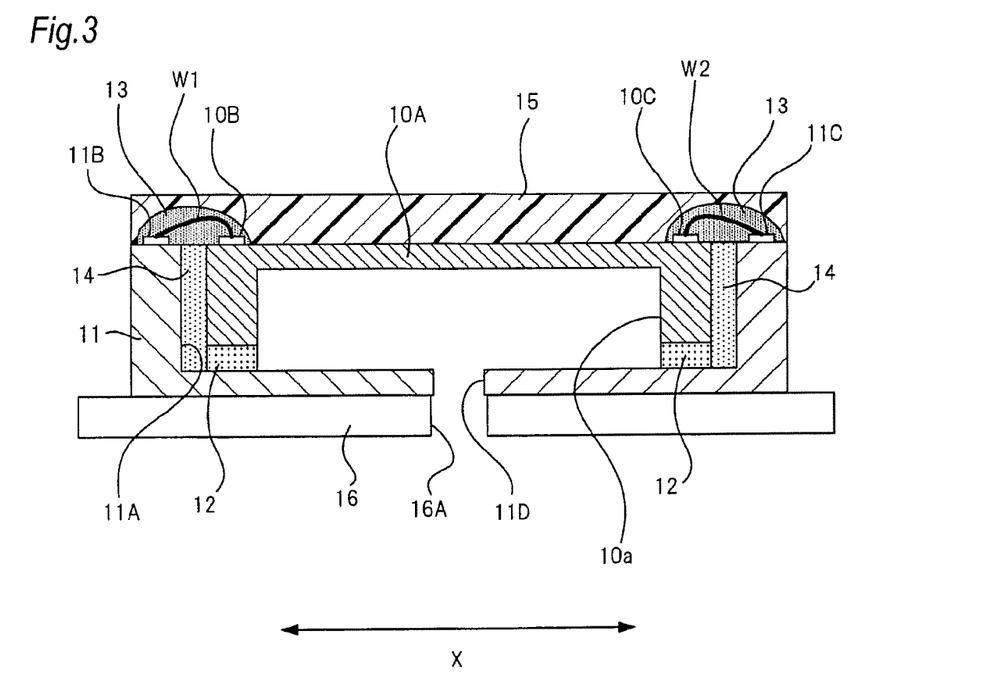
FIG. 3 is a sectional schematic view taken along line A-A of FIG. 2.
Figure 4:
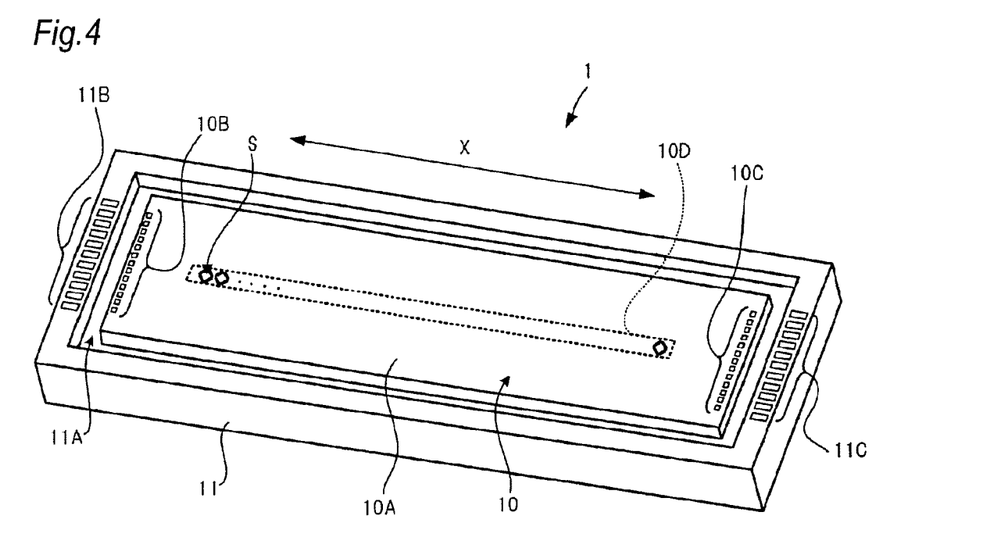
FIG. 4 is a perspective view showing the configuration of main portions as seeing the pressure pulse wave sensor 1 from a side which is to be in contact with the skin.

FIG. 3 is a sectional schematic view taken along line A-A shown in FIG. 2. FIG. 4 is a perspective view showing the configuration of main portions as seeing the pressure pulse wave sensor 1 from the side which is to be in contact with the skin. In FIG. 4, illustration of partial components is omitted. In FIG. 3, the components other than the flexible substrate 16 constitute the pressure pulse wave sensor 1.

As shown in FIG. 4, the pressure pulse wave sensor 1 includes a sensor chip 10, and a container-like substrate 11 which as a concave portion 11A, and in which the sensor chip 10 is fixed to the bottom surface of the concave portion 11A.

The sensor chip 10 includes a semiconductor substrate 10A made of a single crystal of silicon, that of a compound semiconductor such as gallium arsenide, or the like. The semiconductor substrate 10A is formed into a rectangular shape in which the direction X coincides with the longitudinal direction.

The substrate 11 is configured by a rigid substrate which is sufficiently higher in rigidity than the semiconductor substrate 10A, such as a ceramic substrate, a glass substrate, or the like. The substrate 11 is formed into a rectangular shape in which the direction X coincides with the longitudinal direction.

As shown in FIG. 4, a plurality of pressure-sensitive elements S each of which is configured by a bridge having four piezoresistance portions, and which are used for sensing a contact pressure are arranged along the direction X on the surface (the surface on the side which is to be in contact with the skin of a living body) of the semiconductor substrate 10A. A pressure-sensitive element row 10D is configured by the plurality of pressure-sensitive elements S which are arranged in the direction X. In FIG. 3, illustration of the pressure-sensitive elements S is omitted.

In the semiconductor substrate 10A, in the surface opposite to the surface (hereinafter, referred to as the pressure-sensitive surface) on which the pressure-sensitive element row 10D is formed, as shown in FIG. 3, a concave portion 10a which is recessed in the direction (hereinafter, referred to as the sensor pressing direction) perpendicular to the pressure-sensitive surface is formed.

The concave portion 10a causes the semiconductor substrate 10A to have a configuration including a thin portion (diaphragm) in which the thickness in the sensor pressing direction is smaller than that of the other portion. Then, the pressure-sensitive element row 10D is formed in a region of the pressure-sensitive surface which is on the side opposite to the bottom surface of the concave portion 10a.

A portion which is of the surface opposite to the pressure-sensitive surface of the semiconductor substrate 10A, and which is other than the concave portion 10a (in other words, the surface in which the concave portion 10a is formed) is fixed to the bottom surface of the concave portion 11A of the substrate 11 by an adhesive material 12. As the adhesive material 12, for example, an ultraviolet curable resin is used.

The semiconductor substrate 10A is fixed to the bottom surface of the concave portion 11A of the rigid substrate 11 so that the concave portion 10a of the semiconductor substrate 10A communicates with the atmosphere only through a through hole 11D which is formed in the bottom surface of the concave portion 11A of the rigid substrate 11.

One pressure pulse wave sensor 1 of the two pressure pulse wave sensors 1 of the blood pressure measurement device 100 is mounted on the flexible substrate 16 so that the through hole 11D and the through hole 16A overlap with each other in a plan view as seen from the side of the pressure-sensitive surface. The other pressure pulse wave sensor 1 of the two pressure pulse wave sensors 1 of the blood pressure measurement device 100 is mounted on the flexible substrate 16 so that the through hole 11D and the through hole 16B overlap with each other in the plan view.

According to this configuration, a space which is in the pressure pulse wave sensor 1, and which is defined by the semiconductor substrate 10A, the adhesive material 12, and the substrate 11 is kept at atmospheric pressure (reference pressure) by the through hole 11D of the substrate 11, and the through hole 16A (or the through hole 16B) of the flexible substrate 16.

A first terminal portion 10B and second terminal portion 10C which are electrically connected to the pressure-sensitive element row 10D are placed in both end portions of the pressure-sensitive surface of the semiconductor substrate 10A in the direction X. Each of the first terminal portion 10B and the second terminal portion 10C is configured by a plurality of electrode pads which are arranged in a direction Y that is perpendicular to the direction X.

In the pressure pulse wave sensor 1, as shown in FIG. 3, the pressure-sensitive surface of the semiconductor substrate 10A, and the surface of the substrate 11 in which the concave portion 11A is formed are at the same height with respect to the bottom surface of the concave portion 11A of the substrate 11 in the direction perpendicular to the pressure-sensitive surface. The pressure-sensitive surface of the semiconductor substrate 10A, and the surface of the substrate 11 in which the concave portion 11A is formed may not be at the strictly same height, and may have a tolerance.

A third terminal portion 11B for being electrically connected to the first terminal portion 10B, and a fourth terminal portion 11C for being electrically connected to the second terminal portion 10C are disposed on the surface of the substrate 11 in which the concave portion 11A is formed.

In a plan view as seen in the direction perpendicular to the pressure-sensitive surface of the semiconductor substrate 10A, the third terminal portion 11B, the first terminal portion 10B, the second terminal portion 10C, and the fourth terminal portion 11C are arranged in this order along the direction X.

Each of the third terminal portion 11B and the fourth terminal portion 11C is configured by a plurality of electrode pads which are arranged in the direction Y that is perpendicular to the direction X. Each of the terminals of the third terminal portion 11B corresponds to one of the terminals of the first terminal portion 10B. Each of the terminals of the fourth terminal portion 11C corresponds to one of the terminals of the second terminal portion 10C.

As shown in FIG. 3, the terminals of the first terminal portion 10B are electrically connected to those of the third terminal portion 11B corresponding thereto by wires W1 which are the first electroconductive members. Moreover, the terminals of the second terminal portion 10C are electrically connected to those of the fourth terminal portion 11C corresponding thereto by wires W2 which are the second electroconductive members.

In the substrate 11, although not shown, connection terminals which are connected to the terminals of the third terminal portion 11B, and connection terminals which are connected to the terminals of the fourth terminal portion 11C are exposedly disposed on the surface on the side of the flexible substrate 16. These connection terminals are connected to wiring terminals of the flexible substrate 16.

The peripheries of the wires W1 and the wires W2 are separately covered and protected by protective members 13. A resin such as an epoxy or silicone resin is used as the protective members 13. As the resin material for protecting the wires, a resin which is largely changed in volume depending on environmental conditions such as the temperature and the humidity is often used.

The gap between side surface of the concave portion 11A of the substrate 11, and the semiconductor substrate 10A and the adhesive material 12 is filled with a material 14 which is less changed in volume than the protective members 13 depending on the temperature and the humidity. As the material 14, for example, a resin such as a silicone resin is used.

The pressure-sensitive surface of the semiconductor substrate 10A, the protective member 13 for the wires W1, and the protective member 13 for the wires W2 are covered by a surface coating layer 15 for protecting the surface of the pressure pulse wave sensor 1. The surface coating layer 15 is configured by, for example, a silicone resin.

The thus configured pressure pulse wave sensor 1 is used while the pressure-sensitive surface of the semiconductor substrate 10A on which the pressure-sensitive element row 10D is formed is pressed through the surface coating layer 15 against the body surface of a living body in a state where the pressure-sensitive element row 10D is located directly above an artery, and the direction X intersects (preferably, is perpendicular to) the traveling direction of the artery. From each of the pressure-sensitive elements S, therefore, an electric signal corresponding to distortion applied to the thin portion of the semiconductor substrate 10A, i.e., a signal indicating the pressure variation acting on the pressure-sensitive element S is output.

In the blood pressure measurement device 100, the controller 3 determines the optimum pressure-sensitive element and the optimum pressing force based on the signals output from the pressure pulse wave sensor 1, while adjusting the state of the pressurization which is applied on the body surface through the pressure pulse wave sensor 1 by the pressing mechanism 2. Thereafter, the controller measures the pressure pulse wave based on the signal which is output from the optimum pressure-sensitive element at the optimum pressing force, and calculates biological information such as the blood pressure value and the pulse rate based on the pressure pulse wave.

In the pressure pulse wave sensor, with respect to the bottom surface of the concave portion 11A, as described above, the height of the pressure-sensitive surface on which the first terminal portion 10B and the second terminal portion 10C are formed, and that of the surface of the substrate 11 on which the third terminal portion 11B and the fourth terminal portion 11C are formed are substantially equal to each other.

As compared with the conventional configuration where the sensor chip 10 is fixed to a planar substrate, therefore, the wires W1 and the wires W2 can be shortened in length. As a result, the amount of the material of the protective members 13 for covering the wires W1, W2 can be reduced.

As described above, a material which is largely changed in volume depending on changes of the temperature and the humidity is often used in the protective members 13. According to the pressure pulse wave sensor 1, the amount of the material can be reduced, and, even when a volume change occurs in the protective members 13 depending on the environmental conditions, therefore, the influence of a stress due to the volume change on the sensor chip 10 can be made small. Consequently, the accuracy of detecting a pressure pulse wave can be prevented from being lowered due to a change of the use environment.

The pressure pulse wave sensor 1 has the configuration where the protective members 13 are disposed in the both end sides in the direction X of the pressure-sensitive element row 10D. Therefore, the detection sensitivities of the pressure-sensitive elements S of the pressure-sensitive element row 10D are varied as shown in FIG. 5 by the influence of a stress of the protective members 13.

Figure 5:
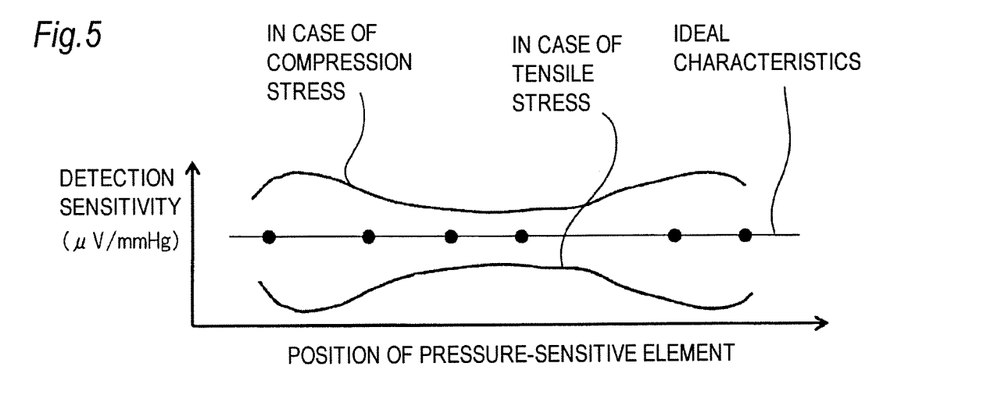
FIG. 5 is a view illustrating an influence of a stress due to a protective member 13.

FIG. 5 shows ideal sensitivity characteristics in which the detection sensitivities of the pressure-sensitive elements S are constant, sensitivity characteristics of the pressure-sensitive element row 10D in the case where a compression stress is generated by the protective members 13, and those of the pressure-sensitive element row 10D in the case where a tensile stress is generated by the protective members 13.

In the configuration where the protective members 13 are disposed in the both end sides in the direction X of the pressure-sensitive element row 10D, as in the pressure pulse wave sensor 1, it is seen that a stress produced by deformation of the protective members 13 causes sensitivities to be dispersed between the pressure-sensitive elements S which are located close to the protective members 13, and the pressure-sensitive elements S which are located remote from the protective members 13.

For example, the sensor chip disclosed in JP-A-2004-188183 has the configuration where the wiring protective member is disposed on the both sides of each of the pressure-sensitive elements of the pressure-sensitive element row.

According to the configuration, the pressure-sensitive elements are affected in an approximately same manner by a stress produced by deformation of the wiring protective member. Even when the volume of the wiring protective member is largely changed, therefore, the detection sensitivity dispersion in the pressure-sensitive element row can be set within an allowable range.

By contrast, the pressure pulse wave sensor 1 has the configuration where the protective members 13 are disposed on the both sides in the direction X of the pressure-sensitive element row 10D. As shown in FIG. 5, therefore, the manner in which a stress is applied to the respective pressure-sensitive elements is largely varied depending on the position. Consequently, the configuration of the embodiment in which the volume change in the protective members 13 can be remarkably reduced is very effective.

In the configuration of the pressure pulse wave sensor 1, moreover, the wires and the protective members do not exist in portions where the sensor may possibly overlap with an artery, and the portions are flat. Therefore, a pressure pulse wave is easily transmitted to the pressure-sensitive element row 10D, and the accuracy of detecting a pressure pulse wave can be improved.

In the pressure pulse wave sensor 1, moreover, the gaps between the end surfaces in the direction X of the sensor chip 10 and the substrate 11 are filled with the material 14 which is less changed in volume than the protective members 13 depending on the temperature and the humidity.

According to the configuration, an influence of a stress which is caused by distortion of the substrate 11, and which acts on the sensor chip 10 can be weakened by the material 14.

Since the gaps are filled with the material 14, the material of the protective members 13 does not flow in the gaps when the protective members 13 are formed. As compared with a configuration where the material 14 is not used, therefore, the use amount of the material of the protective members 13 can be reduced, and the accuracy of detecting a pressure pulse wave can be prevented from being lowered.

In the case of a configuration where the material 14 is not used, the sensor chip 10 must be fixed to the substrate 11 in order to minimize the gaps between the sensor chip 10 and the substrate 11. Therefore, the accuracy of fixation of the sensor chip 10 to the substrate 11, and the dimension accuracies of the sensor chip 10 and the substrate 11 are required to be high, and the production cost of a pressure pulse wave sensor is increased.

In the pressure pulse wave sensor 1, the fixation accuracy and the dimension accuracies may not be so high, and therefore the production cost can be prevented from being increased.

In the example of FIG. 3, it is assumed that, with respect to the bottom surface of the concave portion 11A, the height of the pressure-sensitive surface on which the first terminal portion 10B and the second terminal portion 10C are formed, and that of the surface of the substrate 11 on which the third terminal portion 11B and the fourth terminal portion 11C are formed are substantially equal to each other. However, the invention is not limited to this configuration.

With respect to the bottom surface of the concave portion 11A, for example, the height of the pressure-sensitive surface on which the first terminal portion 10B and the second terminal portion 10C are formed may be larger than that of the surface of the substrate 11 on which the third terminal portion 11B and the fourth terminal portion 11C are formed.

Alternatively, with respect to the bottom surface of the concave portion 11A, the height of the pressure-sensitive surface on which the first terminal portion 10B and the second terminal portion 10C are formed may be smaller than that of the surface of the substrate 11 on which the third terminal portion 11B and the fourth terminal portion 11C are formed.

In the conventional configuration where the sensor chip 10 is fixed to the planar substrate, the distance between the surface of the sensor chip 10 and the substrate surface is about 400 μm.

In the pressure pulse wave sensor 1, when, with respect to the bottom surface of the concave portion 11A, the difference between the height of the pressure-sensitive surface on which the first terminal portion 10B and the second terminal portion 10C are formed, and that of the surface of the substrate 11 on which the third terminal portion 11B and the fourth terminal portion 11C are formed is sufficiently smaller than 400 μm (preferably, zero), the volume of the protective members 13 can be reduced, and an influence of a stress which acts on the accuracy of detecting a pressure pulse wave can be weakened.

The pressure pulse wave sensor 1 has a configuration where, in both end portions in the direction X of the pressure-sensitive surface of the semiconductor substrate 10A, chip-side terminal portions configured by the first terminal portion 10B and the second terminal portion 10C are disposed, and substrate-side terminal portions configured by the third terminal portion 11B and fourth terminal portion 11C which correspond respectively to the first terminal portion 10B and the second terminal portion 10C are disposed.

Figure 6:
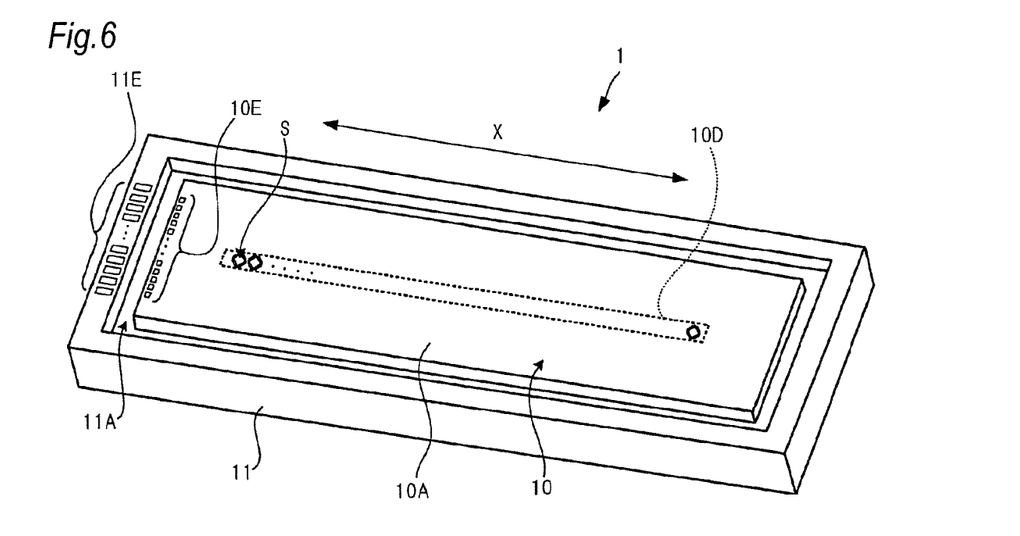
FIG. 6 is a view showing a modification of the perspective view of the pressure pulse wave sensor 1 shown in FIG. 4.

As a modification of the configuration, as shown in FIG. 6, a configuration where a chip-side terminal portion 10E configured by terminals which are electrically connected to the pressure-sensitive elements S is disposed in only one of both end portions in the direction X of the pressure-sensitive surface of the semiconductor substrate 10A may be employed.

In this case, a substrate-side terminal portion 11E configured by terminals for being electrically connected to terminals of the chip-side terminal portion 10E may be formed on the surface which is on the side opposite in the direction X to the pressure-sensitive element row 10D while setting the chip-side terminal portion 10E as a boundary, and in which the concave portion 11A of the substrate 11 is formed.

Also in the case of the configuration of FIG. 6, when a protective member which covers electroconductive members connecting the chip-side terminal portion 10E with the substrate-side terminal portion 11E has a large volume, there is a possibility that a stress produced by deformation of the protective members causes sensitivities to be dispersed between the pressure-sensitive elements S which are located close to the protective members 13, and the pressure-sensitive elements S which are located remote from the protective members 13. Therefore, the configuration of the invention in which the volume of the protective members can be reduced is effective.

In the configuration where, as shown in FIG. 4, the chip-side terminal portions configured by the first terminal portion 10B and the second terminal portion 10C are disposed in the both end portions of the pressure-sensitive surface of the semiconductor substrate 10A in the direction X, the width in the direction Y of the sensor chip 10 is not required to be made so large. Therefore, the configuration is advantageous to miniaturize the pressure pulse wave sensor 1.

The presently disclosed embodiment should be considered in all respects to be illustrative and not restrictive. The scope of the invention is indicated by the appended claims rather than the foregoing description, and all changes which come within the meaning and range of equivalents thereof are intended to be embraced therein.

In the above, for example, the blood pressure measurement device of the wrist wearing type which detects the pressure pulse wave of the radial artery in the wrist has been described. Alternatively, a measurement device which is to be applied to the carotid artery or the dorsalis pedis artery may be possible.

The pressure-sensitive elements S which detect a contact pressure are not limited to elements in which a bridge circuit and a diaphragm are employed, and may use elements having another well-known configuration. The blood pressure measurement device 100 includes the two pressure pulse wave sensors 1. When at least one pressure pulse wave sensor 1 is provided, the pressure pulse wave can be detected, and biological information can be measured.

The substrate 11 may have a structure in which, among the side walls of the concave portion 11A, the side walls at the both ends in the direction Y are removed away. Namely, the substrate 11 may have a substantially U-like shape.

When, as shown in FIG. 4, the concave portion 11A has a rectangular parallelepiped shape, and the substrate 11 is formed into a container-like shape, there is no fear that the material 14 leaks to the outside in a step of filling the gaps between the substrate 11 and the sensor chip 10 with the material 14. Therefore, the pressure pulse wave sensor 1 can be easily produced.

The means for connecting the terminals of the first terminal portion 10B with those of the third terminal portion 11B which corresponds to it is not limited to wires, and may be electroconductive members such as electroconductive paste. Similarly, the means for connecting the terminals of the second terminal portion 10C with those of the fourth terminal portion 11C which corresponds to it is not limited to wires, and may be electroconductive members such as electroconductive paste. Even in a case where the connections are performed by using any kind of electroconductive members, the protective members 13 for protecting the wirings formed by the electroconductive members are necessary, and therefore the invention is effective.

The pressure pulse wave sensor 1 may have a configuration where only the gaps between the end surfaces of the sensor chip 10 in the direction X and the substrate 11 are filled with the material 14. When the gaps are filled with the material 14, in the formation of the protective members 13, it is possible to attain an effect that the volume increase of the protective members 13 due to the flowing of the protective members 13 in the gaps can be prevented from occurring.

As described above, the following matters are disclosed in the description.

The disclosed pressure pulse wave sensor includes: a sensor chip which includes: a pressure-sensitive element row configured by a plurality of pressure-sensitive elements that are arranged in one direction; and a chip-side terminal portion that is placed in an end portion in the one direction of a pressure-sensitive surface on which the pressure-sensitive element row is formed, and that is electrically connected to the pressure-sensitive element row, the sensor chip to be used while the pressure-sensitive surface is pressed against a body surface of a living body in a state where the one direction intersects a traveling direction of an artery of the living body; and a substrate which includes a concave portion, the sensor chip fixed to a bottom surface of the concave portion, a substrate-side terminal portion for being electrically connected to the chip-side terminal portion is disposed on a surface of the substrate in which the concave portion is formed, and the pressure pulse wave sensor further includes: an electroconductive member which connects the chip-side terminal portion and the substrate-side terminal portion to each other; and a protective member which covers the electroconductive member.

In the disclosed pressure pulse wave sensor, the chip-side terminal portion is configured by a first terminal portion and second terminal portion which are placed in both end portions in the one direction of a pressure-sensitive surface, respectively, the substrate-side terminal portion is configured by a third terminal portion for being electrically connected to the first terminal portion, and a fourth terminal portion for being electrically connected to the second terminal portion, in a plan view as seen in a direction perpendicular to the pressure-sensitive surface, the third terminal portion, the first terminal portion, the second terminal portion, and the fourth terminal portion are arranged in this order along the one direction, the electroconductive member is configured by a first electroconductive member which connects the first terminal portion and the third terminal portion to each other, and a second electroconductive member which connects the second terminal portion and the fourth terminal portion to each other, and the protective member covers the first electroconductive member and the second electroconductive member in a separate manner.

In the disclosed pressure pulse wave sensor, with respect to the bottom surface of the concave portion, a height of the pressure-sensitive surface on which the chip-side terminal portion is formed, and a height of the surface of the substrate on which the substrate-side terminal portion is formed are equal to each other.

In the disclosed pressure pulse wave sensor, a gap between an end surface in the one direction of the sensor chip and the substrate is filled with a material which is less changed in volume than the protective member depending on a temperature and a humidity.

The disclosed biological information measurement device includes: the pressure pulse wave sensor; and a biological information calculating section which is configured to calculate biological information based on a pressure pulse wave detected by the pressure pulse wave sensor.

According to the invention, it is possible to provide a pressure pulse wave sensor in which the accuracy of detecting a pressure pulse wave can be prevented from being lowered due to a change of the use environment, and a biological information measurement device which includes the sensor.

Although the invention has been described with reference to the specific embodiment, the invention is not limited to the embodiment, and various changes can be made without departing from the technical spirit of the disclosed invention.

What is claimed is:

1. A pressure pulse wave sensor comprising:
   a sensor chip which includes a semiconductor substrate including:
   a pressure-sensitive element row configured by a plurality of pressure-sensitive elements that are arranged in one direction; and
   a first chip-side terminal portion that is placed in one end portion in the one direction of a pressure-sensitive surface on which the pressure-sensitive element row is formed, and that is electrically connected to the pressure-sensitive element row, the semiconductor substrate further including a thin portion in which a thickness in a direction perpendicular to the pressure-sensitive surface is smaller than a thickness of an other portion of the semiconductor substrate, the sensor chip to be used while the pressure-sensitive surface is pressed against a body surface of a living body in a state where the one direction intersects a traveling direction of an artery of the living body; and
   a substrate which includes a first concave portion, the semiconductor substrate of the sensor chip fixed to a bottom surface of the first concave portion,
   wherein a first substrate-side terminal portion for being electrically connected to the first chip-side terminal portion is disposed on a surface of a side wall of the first concave portion of the substrate, the surface being at a predetermined height with respect to the bottom surface of the first concave portion,
   wherein the pressure pulse wave sensor further comprises:
   a first electroconductive member connecting the first chip-side terminal portion and the first substrate-side terminal portion to each other; and
   a first protective member covering the first electroconductive member,
   wherein a gap is formed between an end surface in the one direction of the sensor chip and the surface of the side wall of the first concave portion of the substrate and the gap is filled with a material which changes less in volume than the first protective member depending on a temperature and a humidity,
   wherein in the semiconductor substrate, a second concave portion is formed in a surface opposite to the pressure-sensitive surface, and
   wherein the first concave portion and the second concave portion are opened in opposite directions with respect to each other.

2. The pressure pulse wave sensor according to claim 1, further comprising:
   a second chip-side terminal portion that is placed in another end portion in the one direction of the pressure-sensitive surface, and that is electrically connected to the pressure-sensitive element row;
   a second substrate-side terminal portion for being electrically connected to the second chip-side terminal portion,
   wherein the second substrate-side terminal portion is disposed on a surface of another side wall of the first concave portion of the substrate, the surface being at the predetermined height with respect to the bottom surface of the first concave portion,
   wherein in a plan view as seen in a direction perpendicular to the pressure-sensitive surface, the first substrate-side terminal portion, the first chip-side terminal portion, the second chip-side terminal portion, and the second substrate-side terminal portion are arranged in this order along the one direction,
   a second electroconductive member connecting the second chip-side terminal portion and the second substrate-side terminal portion to each other; and
   a second protective member covering the second electroconductive member.

3. The pressure pulse wave sensor according to claim 1, wherein,
   with respect to the bottom surface of the first concave portion, a height of the pressure-sensitive surface on which the first chip-side terminal portion is formed, and a height of the surface of the substrate on which the first substrate-side terminal portion is disposed are equal to each other.

4. A biological information measurement device comprising:
- a pressure pulse wave sensor,
- wherein the pressure pulse wave sensor comprising:
  - a sensor chip which includes a semiconductor substrate including:
    - a pressure-sensitive element row configured by a plurality of pressure-sensitive elements that are arranged in one direction; and
    - a first chip-side terminal portion that is placed in one end portion in the one direction of a pressure-sensitive surface on which the pressure-sensitive element row is formed, and that is electrically connected to the pressure-sensitive element row, the semiconductor substrate further including a thin portion in which a thickness in a direction perpendicular to the pressure-sensitive surface is smaller than a thickness of an other portion of the semiconductor substrate, the sensor chip to be used while the pressure-sensitive surface is pressed against a body surface of a living body in a state where the one direction intersects a traveling direction of an artery of the living body; and
  - a substrate which includes a first concave portion, the semiconductor substrate of the sensor chip fixed to a bottom surface of the first concave portion,
- wherein a first substrate-side terminal portion for being electrically connected to the first chip-side terminal portion is disposed on a surface of a side wall of the first concave portion of the substrate, the surface being at a predetermined height with respect to the bottom surface of the first concave portion,
- wherein the pressure pulse wave sensor further comprises:
  - a first electroconductive member connecting the first chip-side terminal portion and the first substrate-side terminal portion to each other; and
  - a first protective member covering the first electroconductive member,
  - wherein a gap is formed between an end surface in the one direction of the sensor chip and the surface of the side wall of the first concave portion of the substrate and the gap is filled with a material which changes less in volume than the first protective member depending on a temperature and a humidity,
  - wherein in the semiconductor substrate, a second concave portion is formed in a surface opposite to the pressure-sensitive surface, and
  - wherein the first concave portion and the second concave portion are opened in opposite directions with respect to each other.

5. The pressure pulse wave sensor according to claim 1, wherein the first protective member is an epoxy or silicone resin.

6. The pressure pulse wave sensor according to claim 2, wherein the first protective member and second protective member are an epoxy or silicone resin.

7. The biological information measurement device of claim 4, wherein the pressure pulse wave sensor further comprises:
- a second chip-side terminal portion that is placed in another end portion in the one direction of the pressure-sensitive surface, and that is electrically connected to the pressure-sensitive element row;
- a second substrate-side terminal portion for being electrically connected to the second chip-side terminal portion,
- wherein the second substrate-side terminal portion is disposed on a surface of another side wall of the first concave portion of the substrate, the surface being at the predetermined height with respect to the bottom surface of the first concave portion,
- wherein in a plan view as seen in a direction perpendicular to the pressure-sensitive surface, the first substrate-side terminal portion, the first chip-side terminal portion, the second chip-side terminal portion, and the second substrate-side terminal portion are arranged in this order along the one direction,
- a second electroconductive member connecting the second chip-side terminal portion and the second substrate-side terminal portion to each other; and
- a second protective member covering the second electroconductive member.

8. The biological information measurement device according to claim 4, wherein, with respect to the bottom surface of the first concave portion, a height of the pressure-sensitive surface on which the first chip-side terminal portion is formed, and a height of the surface of the substrate on which the first substrate-side terminal portion is disposed are equal to each other.

9. The biological information measurement device according to claim 4, wherein the first protective member is an epoxy or silicone resin.

10. The biological information measurement device according to claim 7, wherein the first protective member and second protective member are an epoxy or silicone resin.

11. The biological information measurement device according to claim 1, wherein the semiconductor substrate is fixed to the bottom surface of the first concave portion so that the second concave portion communicates with atmosphere only through a through hole which is formed in the bottom surface of the first concave portion.

12. The biological information measurement device according to claim 4, wherein the semiconductor substrate is fixed to the bottom surface of the first concave portion so that the second concave portion communicates with atmosphere only through a through hole which is formed in the bottom surface of the first concave portion.

* * * * *